US00PP35812P3

(12) United States Plant Patent
Olesen

(10) Patent No.: US PP35,812 P3
(45) Date of Patent: May 21, 2024

(54) HYBRID TEA ROSE PLANT NAMED 'POULREN047'

(50) Latin Name: *Rosa hybrida*
Varietal Denomination: Poulren047

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 18/445,492

(22) Filed: Sep. 8, 2023

(65) Prior Publication Data

US 2024/0107924 P1 Mar. 28, 2024

(30) Foreign Application Priority Data

Sep. 30, 2022 (QZ) ..... PBR 2022/2158

(51) Int. Cl.
*A01H 5/02* (2018.01)
*A01H 6/74* (2018.01)

(52) U.S. Cl.
USPC ..... Plt./130

(58) Field of Classification Search
USPC ..... Plt./130, 148, 137, 107, 141, 102
CPC . A01H 5/02; A01H 5/00; A01H 6/749; A01H 6/74
See application file for complete search history.

(56) References Cited

U.S. PATENT DOCUMENTS

PP26,569 P3 * 4/2016 Olesen ..... A01H 6/749 Plt./108

OTHER PUBLICATIONS

CPVO Register Version 4.12.16 retrieved on Nov. 27, 2023 at https://online.plantvarieties.eu/publicConsultationDetails?registerId=20222158&denomination=poulren047, 2 pp. (Year: 2023).*

* cited by examiner

*Primary Examiner* — June Hwu

(57) ABSTRACT

A new garden rose plant of the Hybrid Tea class which has abundant, mauve flowers and attractive foliage. This new and distinct variety has shown to be uniform and stable in the resulting generations from asexual propagation.

2 Drawing Sheets

Botanical designation: *Rosa hybrida.*
Variety denomination: 'Poulren047'.

This application claims priority to Plant Breeder's Rights Application Number 2022/2158, which was filed at the Community Plant Variety Rights Office in the European Union on Sep. 30, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2014 and the resulting seeds were planted in a controlled environment in Fredensborg, Denmark. The new variety, named 'Poulren047', originated as a single seedling from the stated cross.

The new variety may be distinguished from its male pollen parent and female seed parent primarily by the following characteristics. The male pollen parent plant has white flowers while the new variety has mauve flowers. The female seed parent plant has dark red flowers while the new variety has mauve flowers.

The objective of the hybridization of this rose variety was to create a new and distinct variety with unique qualities, such as:

1. Uniform and abundant, mauve, perfumed flowers;
2. Vigorous, but compact growth when propagated on its own roots;
3. Exceptional disease resistance.

This combination of qualities is not present in previously available commercial cultivars of this type, known to the inventor, and distinguish 'Poulren047' from all other varieties of which we are aware.

As part of the rose development program, Mogens N. Olesen germinated the seeds from the aforementioned hybridization during winter of 2014 and conducted evaluations on the resulting seedlings in a controlled environment in Fredensborg, Denmark. 'Poulren047' was selected in the spring of 2015 by the inventor as a single plant from the progeny of the aforementioned hybridization.

Asexual reproduction of 'Poulren047' by rooted cuttings was first done by Mogens N. Olesen in the nursery in Fredensborg, Denmark in July, 2015. This initial and other subsequent asexual propagations conducted in controlled environments have demonstrated that the characteristics of 'Poulren047' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren047'.

Specifically illustrated in FIG. 1 of the drawings are open flowers viewed from above and the side, a cluster of flower buds and partially open flowers on a branch, sepals detached revealing reproductive flower parts and petals detached.

Figure 1:
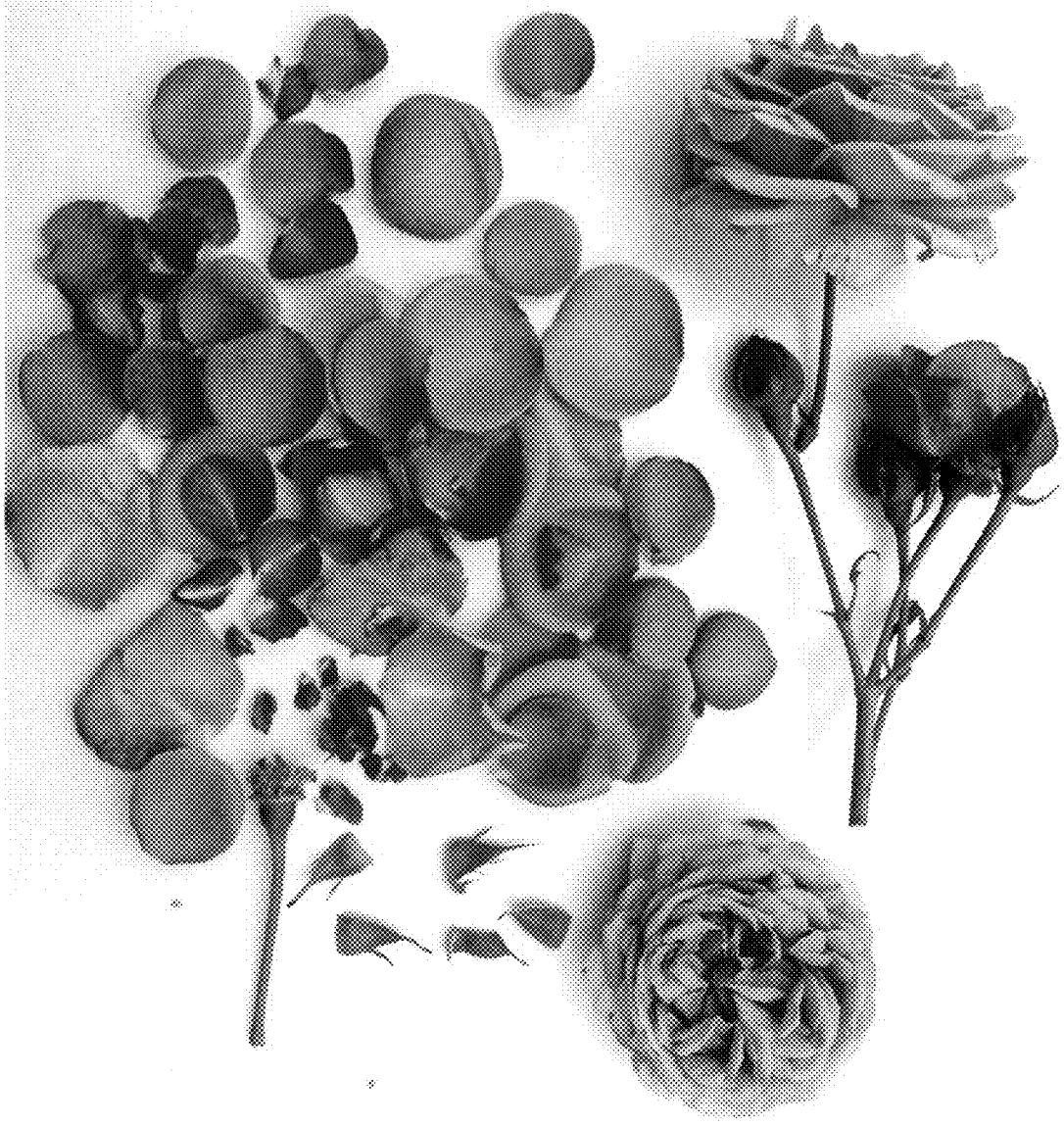
Figure 2:
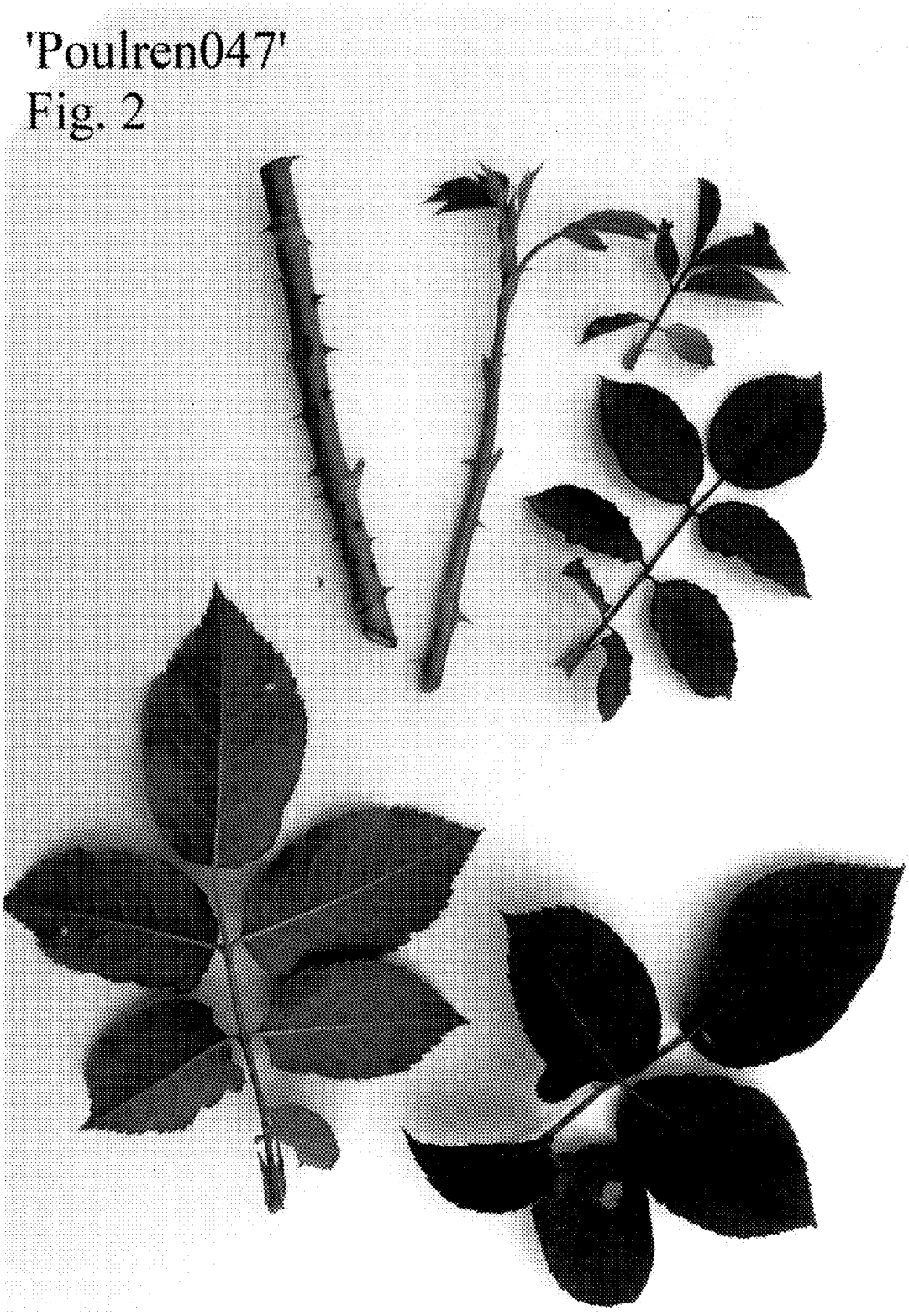

Specifically illustrated in FIG. 2 of the drawings are a mature and juvenile bare stem exhibiting prickles, juvenile leaves exhibiting anthocyanin, and mature leaves viewed from above and underneath.

Plants shown are 15 months old.

DETAILED DESCRIPTION OF THE VARIETY

The following is a description of 'Poulren047', as observed in its growth in an outdoor nursery in Odense Denmark. Observed plants are 15 months of age, and were grown on their own roots in 30 cm pots. Color references are made using The Royal Horticultural Society (London, England) Colour Chart, 2001, except where common terms of color are used.

For a comparison, several physical characteristics of the rose variety 'Poulren014', U.S. Plant Pat. No. 26,569 are compared to the claimed plant. While 'Poulren047' has 65 flower petals, 'Poulren014' has 90 flower petals. Open flowers of 'Poulren047' have a general tonality of Purple Group 75B and 75C while 'Poulren014' has a general tonality of Red-Purple Group 67A with intonations of Red-Purple Group 71C. Juvenile foliage of the claimed plant tends to be Yellow-Green with anthocyanin on the margins, while the comparison variety has juvenile foliage which is completely greyed purple.

FLOWER AND FLOWER BUD

Blooming habit: Continuous.

Flower bud:

- *Size*.—Upon opening, 27 mm in length from base of receptacle to end of bud. Bud diameter is 16 mm.
- *Bud form*.—Ovoid.
- *Bud color*.—As sepals divide petals are Red-Purple Group 64B.
- *Sepal inner surface*.—Color: Yellow-Green Group 146D. Surface: Lightly pubescent.
- *Sepal outer surface*.—Color: Yellow-Green Group 144A with intonations of Greyed-Red Group 180A. Texture: Smooth.
- *Sepal shape*.—Apex: Cirrhose. Base: Flat at union with receptacle.
- *Sepal margin*.—Margins have weak foliaceous appendages on three of the five sepals.
- *Sepal size*.—About 28 mm long, 10 mm wide.
- *Receptacle*.—Texture: Smooth. Size: 10 mm in height, 10 mm wide. Color: Yellow-Green Group 144A. Shape: Campanulate.
- *Pedicel*.—Surface: Smooth. Length: About 60 mm. Diameter: 3 mm on average. Color: Yellow-Green Group 145A. Strength: Strong.
- *Peduncle*.—Length: 20 to 25 mm. Diameter: About 3 or 4 mm. Color: Yellow-Green Group 145A. Texture: Smooth.

Flower bud development: Flower buds are borne in clusters of 5 flower buds per stem.

Flower bloom:

- *Fragrance*.—Strong perfume with hints of citrus.
- *Duration*.—The blooms have a duration on the plant of approximately 19 days. Petals fall cleanly away from plant after flowers have fully matured.
- *Size*.—Flower diameter is 90 mm when open. Flower depth is 40 mm.
- *Flower shape*.—Quartered-rosette, very double, with many overlapping petals packed into quarter sections.
- *Shape of flower, side view*.—The upper portion is flat convex. The lower portion is concave.

Petalage: Under normal conditions, flowers have about 65 petals.

General tonality of flower: Open flowers are Purple Group 75B and 75C.

Petal color:

- *Upon opening, outer petals*.—Upper surface: Red-Purple Group 64D at marginal zone. Middle zone Red-Purple Group 64C. Streak of Purple Group 75D. Petal spot at basal zone Yellow Group 1C. Lower surface: Red-Purple Group 64C with streaks of Purple Group 75D. Basal zone spot Yellow-Green Group 145D.
- *Upon opening, inner petals*.—Upper surface: Red-Purple Group 64C. Yellow 1D spot. Lower surface: Red-Purple Group 64B. Yellow 1D spot.
- *After opening, outer petals*.—Upper surface: Red-Purple Group 73D with darker shades of 73B. Basal zone White Group 155D. Lower surface: Red-Purple Group 62B and 62C.
- *After opening, inner petals*.—Upper surface: Red-Purple Group 73A. Lower surface: Red-Purple Group 67C with streaks of White Group 155A. At the basal point of attachment Yellow Group 1D.

Petals:

- *Petal reflex*.—Strong.
- *Margin*.—Irregular with one or more small clefts and strong or moderate undulations.
- *Shape*.—Broad and elliptic. Apex shape: Rounded. Base shape: Acute.
- *Size*.—40 mm (l)×51 mm (w).
- *Texture*.—Smooth.
- *Thickness*.—Average.

Petaloids:

- *Size*.—10 mm (l) by 7 mm (w).
- Quantity.—About 12.
- *Shape*.—Elliptical with an acute base and rounded apex.
- *Color*.—Red-Purple Group 71A on upper and lower surface. Petaloid spot at the basal zone Yellow Group 4B.

Reproductive flower parts:

- *Pollen*.—None observed.
- *Anthers*.—Size: 2 mm in length. Color: Yellow Group 13B. Quantity: 36 on average.
- *Filaments*.—Color: Yellow Group 10C and Red Group 47C. Length: 4 mm.
- *Pistils*.—Length: 4 mm. Quantity: 25 on average.
- *Stigmas*.—Color: Yellow Group 1C.
- *Styles*.—Color: Yellow Group 1C.
- *Location of stigmas*.—Inferior in location relative to the length of the filaments and the height of the anthers.
- *Hips*.—None Observed.

PLANT

Plant growth: Upright. Plants are about 70 cm in height, and 53 cm wide.

Stems:

*Color of juvenile growth*.—Yellow-Green Group 145A.

*Color of mature growth*.—Yellow-Green Group 146B.

*Length*.—Canes are about 28 cm from the base of the plant to the flowering portion.

*Diameter*.—About 10 mm.

*Internodes*.—On mature canes about 45 mm between nodes.

*Surface texture*.—Young wood: Smooth. Older wood: Smooth.

Long prickles:

*Incidence*.—17 prickles per 10 cm of stem.

*Size*.—Average length of prickles on mature stems is 5 mm.

*Shape*.—Upper portion is linear. Lower portion is concave.

*Color*.—Juvenile prickles: Greyed-Red Group 179D. Mature prickles: Greyed-Red Group 180B.

Plant foliage:

*Compound leaf*.—155 mm (l)×135 (w).

*Quantity*.—2 leaves per 10 cm of stem on average.

*Leaf bearing angle to the stem*.—75 degrees.

*Color of juvenile foliage*.—Upper side: Yellow-Green Group 146B with marginal intonations of Greyed-Purple Group 183B. Lower side: Yellow-Green Group 144B.

*Color of mature foliage*.—Upper side: Yellow-Green Group 147A. Lower side: Yellow-Green Group 146A.

Plant leaves and leaflets:

*Stipules*.—Size: 21 mm long, 3 mm wide. Quantity: 2 per compound leaf. Shape: Linear, slightly broad based with outward extending apex. Margins: Finely serrated. Color: Yellow-Green Group 144A.

*Petiole*.—Length: About 30 mm. Diameter: 2 mm. Upper surface color: Yellow-Green Group 144A. Lower surface color: Yellow-Green Group 144A.

*Rachis*.—Length: About 45 mm. Upper surface color: Yellow-Green Group 144A. Lower surface color: Yellow-Green Group 144A. Texture: Small prickles Greyed-Red Group 180A.

*Leaflet*.—Quantity: Normally 5, occasionally 7 leaflets. Margins: Serrated. Size: Terminal leaflets are about 80 mm long, 54 mm wide. Shape: Generally elliptical. Base: Rounded. Apex: Acute. Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulren047' substantially as described and illustrated herein.

* * * * *

'Poulren047'

'Poulren047'